(12) United States Patent
Kambayashi et al.

(10) Patent No.: US 8,927,033 B2
(45) Date of Patent: Jan. 6, 2015

(54) HYPERLIPEMIA-AMELIORATING AGENT, ANEMIA-AMELIORATING COMPOSITION, URIC-ACID-LEVEL-REDUCING COMPOSITION, AND FOOD OR BEVERAGE

(71) Applicants: Hiroaki Kambayashi, Tokyo (JP); Kumiko Kitamura, Tokyo (JP); Hideaki Iwasaki, Tokyo (JP)

(72) Inventors: Hiroaki Kambayashi, Tokyo (JP); Kumiko Kitamura, Tokyo (JP); Hideaki Iwasaki, Tokyo (JP)

(73) Assignee: Lion Corporation, Tokyo (JP)

( * ) Notice: Subject to any disclaimer, the term of this patent is extended or adjusted under 35 U.S.C. 154(b) by 107 days.

(21) Appl. No.: 13/738,234

(22) Filed: Jan. 10, 2013

(65) Prior Publication Data

US 2013/0131025 A1    May 23, 2013

Related U.S. Application Data (60) Division of application No. 13/527,729, filed on Jun. 20, 2012, now abandoned, which is a continuation of application No. PCT/JP2010/067058, filed on Sep. 30, 2010.

(30) Foreign Application Priority Data

Dec. 21, 2009 (JP) ................................ 2009-289798
Jun. 8, 2010 (JP) ................................ 2010-131169

(51) Int. Cl.
| | | |
|---|---|---|
| *A61K 36/258* | (2006.01) | |
| *A61K 36/00* | (2006.01) | |
| *A61K 31/58* | (2006.01) | |
| *A61K 31/575* | (2006.01) | |
| *C07J 9/00* | (2006.01) | |
| *C07J 17/00* | (2006.01) | |
| *A61K 31/57* | (2006.01) | |

(52) U.S. Cl.
CPC .............. *A61K 31/58* (2013.01); *A61K 31/575* (2013.01); *C07J 9/00* (2013.01); *C07J 17/00* (2013.01); *A61K 31/57* (2013.01)
USPC .......................................... 424/728; 424/725

(58) Field of Classification Search
None
See application file for complete search history.

(56) References Cited

U.S. PATENT DOCUMENTS

| 4,317,816 A | 3/1982 | Arichi et al. |
|---|---|---|
| 2005/0287230 A1 | 12/2005 | Young |
| 2008/0234208 A1 | 9/2008 | Sun et al. |

FOREIGN PATENT DOCUMENTS

| CN | 1300594 | 6/2001 |
|---|---|---|
| CN | 1531927 | 9/2004 |
| CN | 101264204 | 9/2008 |
| CN | 101307281 | 11/2008 |
| EP | 1 905 444 | 4/2008 |
| JP | 59-48421 A | 3/1984 |
| JP | 3-9752 A | 1/1991 |
| JP | 8-143465 A | 6/1996 |
| JP | 8-291194 A | 11/1996 |
| JP | 9-208479 A | 8/1997 |
| JP | 2000-502994 | 3/2000 |
| JP | WO 01/43753 A2 | 6/2001 |
| JP | 2002-212085 A | 7/2002 |
| JP | 2002-275086 A | 9/2002 |
| JP | 2002-322068 A | 11/2002 |
| JP | 2002-370980 A | 12/2002 |
| JP | 2003-517016 A | 5/2003 |
| JP | 2004-201598 A | 7/2004 |
| JP | 2005-187405 A | 7/2005 |
| JP | 2006-16340 A | 1/2006 |
| JP | 2007-153888 A | 6/2007 |
| JP | 2009-500432 A | 1/2009 |
| KR | 20030075441 | 9/2003 |
| KR | 10-0678490 | 2/2007 |
| WO | WO 97/18824 | 5/1997 |
| WO | WO 02/067950 A1 | 9/2002 |
| WO | WO 2005/030235 A1 | 4/2005 |

OTHER PUBLICATIONS

Niu et al., *Effect of Panaxadiol Saponin and Panaxtrol Saponin on Proliferation of Human Bone Marrow Hemopoietic Progenitor Cells*, 20(11) Chinese Pharmacological Bulletin 1316-1317 (2004).
Niu et al., *Effects of PDS and PTS on the proliferation of mouse haemopoietic stem/progenitor cells in vitro*, 24(2) Chinese Journal of Integrated Traditional and Western Medicine 127-132 (2004).
Japanese Office Action dated Dec. 17, 2013, issued in corresponding JP 2009-289798 with English translation.
Supplementary European Search Report mailed on Apr. 26, 2013, in EP Patent Application No. 10839037.8—1464/ 2517711.
Hu et al., *Effects of Panaxadiol Saponins on blood glucose and lipid metabolism in experimental hyperglycemia of type 2 diabetes mellitus rats*, 32(6) Journal of Jilin University 1004-1008 (2006).
International Search Report (PCT/ISA/210) issued on Nov. 16, 2010, by the Japanese Patent Office as the International Searching Authority for International Application No. PCT/JP2010/067058.
Written Opinion (PCT/ISA/237) issued on Nov. 16, 2010, by the Japanese Patent Office as the International Searching Authority for International Application No. PCT/JP2010/067058.
Byoung-Mog Kwon et al., *Acyl-CoA: Cholesterol Acyltransferase inhibitory Activity of Ginseng Sapogenins, Produced From the Ginseng Sapogenins, Produced From the Ginseng Saponins*, 9 Bioorganic & Medicinal Chemistry Letters 1375-1378 (1999).

(Continued)

*Primary Examiner* — Qiuwen Mi
(74) *Attorney, Agent, or Firm* — Buchanan, Ingersoll & Rooney, PC (57) ABSTRACT

A neutral-fat-level-regulating agent, a cholesterol-level-regulating agent, a free-fatty-acid-level-regulating agent or an anti-obesity agent, including: at least one of protopanaxatriol, panaxatriol, protopanaxadiol and panaxadiol which are aglycons of dammarane-type saponins and a hyperlipemia-ameliorating agent including: at least one of the neutral-fat-level-regulating agent, the cholesterol-level-regulating agent, the free-fatty-acid-level-regulating agent and the anti-obesity agent.

4 Claims, 1 Drawing Sheet

(56) References Cited

OTHER PUBLICATIONS

Masahiro Yamamoto et al., *Effect of Long Term Administration of Red Ginseng Powder in Patients with Hyperlipidemia*, 16 Proc. Symp. Wakan-Yaku 188-191 (1983).

Chinese Office Action dated Feb. 27, 2014 (mailed on Mar. 4, 2014), issued in corresponding Japanese Patent Application No. 2010-131169, with English translation (mailed on Mar. 4, 2014).

Huh et al., *Effect of Ginseng Saponins on Xanthine Oxidase Activity after Ethanol Treatment in Mouse Liver*, 23(3&4) Yakhak Hoeji 173-179 (1979).

Huh et al., *Effect of Panax Ginseng on Xanthine Oxidase Activity in Ethanol-Induced Hyperuricemia*, Proceedings of the $3^{RD}$ International Ginseng Symposium 131-135 (1980).

Niu et al., *Effects of PDS and PTS on the proliferation of mouse haemopoietic stem/progenitor cells* in vitro, 24(2) Chinese Journal of Integrated Traditional and Western Medicine 172-132 (2004).

Chinese Office Action dated Feb. 7, 2014, issued in corresponding CN Patent Application No. 201080059382.5, with English translation.

Japanese Office Action mailed on Mar. 4, 2014, issued in corresponding Japanese Patent Application No. 2010-131169, with English translation.

HYPERLIPEMIA-AMELIORATING AGENT, ANEMIA-AMELIORATING COMPOSITION, URIC-ACID-LEVEL-REDUCING COMPOSITION, AND FOOD OR BEVERAGE

CROSS-REFERENCE TO RELATED APPLICATIONS

This application is a Divisional Application of U.S. patent application Ser. No. 13/527,729, filed on Jun. 20, 2012, now abandoned, which is a Continuation Application of International Patent Application PCT/JP2010/067058, filed on Sep. 30, 2010, and published as WO 2011/077800 on Jun. 30, 2011, which claims priority to Japanese Patent Application Serial No. 2010-131169, filed on Jun. 8, 2010, and Japanese Patent Application 2009-289798, filed on Dec. 21, 2009.

BACKGROUND OF THE INVENTION

1. Field of the Invention

The present invention relates to a neutral-fat-level-regulating agent, a cholesterol-level-regulating agent, a free-fatty-acid-level-regulating agent, an anti-obesity agent and an anemia-ameliorating composition, each of which contains at least one of protopanaxatriol, panaxatriol, protopanaxadiol and panaxadiol.

The present invention also relates to a hyperlipemia-ameliorating agent containing at least one of the neutral-fat-level-regulating agent, the cholesterol-level-regulating agent, the free-fatty-acid-level-regulating agent and the anti-obesity agent.

The present invention also relates to a uric-acid-level-reducing composition containing residues obtained by treating plants belonging to the genus *Panax* of the family Araliaceae with an acid.

The present invention also relates to a food or beverage containing at least one of the neutral-fat-level-regulating agent, the cholesterol-level-regulating agent, the free-fatty-acid-level-regulating agent, the anti-obesity agent, the anemia-ameliorating composition and the uric-acid-level-reducing composition.

2. Description of the Related Art

In recent years, since Japanese have increased opportunities to eat Western-style diets, the number of patients with diabetes, arterial sclerosis, heart diseases and cerebrovascular disorders has been increasing. The onset of arterial sclerosis has various causes, among which hyperlipemia is known as a main cause.

Blood contains four types of lipids: cholesterol, neutral fat, phospholipid and free fatty acids. Hyperlipemia is a pathological condition where the levels of these lipids, especially the neutral fat level and/or the cholesterol level, are excessively high. Free fatty acids are consumed as energy, but in obese people, an increased amount of free fatty acids is delivered to the liver where they are used to synthesize neutral fat, resulting in an increase in the neutral fat level. The lipids having increased in their levels remain on vascular endothelium to cause arterial sclerosis. However, the obese people do not have any subjective symptoms, and finally do have an attack of cardiac infarction and/or cerebral infarction. In addition, arterial sclerosis deteriorates the condition of high blood pressure and causes kidney diseases and other diseases.

Methods for treating or preventing hyperlipemia are, for example, improvements of lifestyle and drug therapy.

The improvements of lifestyle are, for example, diet therapy and exercise therapy. Obesity causes abnormal lipid metabolism, abnormal-glucose tolerance, and other abnormal conditions, and can accelerate the progress of arterial sclerosis. Thus, importantly, the diet therapy is conducted to normalize the total energy intake, nutrient balances and the cholesterol intake, and the exercise therapy is conducted to keep the body weight normal. However, there is difficulty in selecting optimal methods for diet restriction and exercise therapy, and those receiving such therapies have to continuously and constantly address them.

Administering a drug such as HMG-CoA reductase inhibitor is reported as the above drug therapy. This drug has cholesterol-regulating effects but problematically involves adverse side effects such as hepatic disorder, rhabdomyolysis, an increase in creatine kinase (CPK) level, diarrhea and stomachache.

In addition, there are reports about oral intake of antioxidants such as vitamin E and polyphenol or amino acids such as lysine and proline. These compounds, however, do not have satisfactory preventing and ameliorating effects on hyperlipemia. Furthermore, there are reports about oral intake of plants belonging to the family Araliaceae, especially *Panax notoginseng* (see International Publication No. WO2005/030235 and Japanese Patent Application Laid-Open (JP-A) Nos. 59-48421 and 2004-201598). These plants, however, do not have satisfactory effects.

Thus, at present, keen demand has arisen for the provision of a drug which has neutral-fat-level-regulating effects, cholesterol-level-regulating effects, free-fatty-acid-level-regulating effects and anti-obesity effects, which can ameliorate hyperlipemia, and which is naturally occurring and highly safe and can be given as a food or beverage.

In recent years, there have been various problematic symptoms accompanied by anemia.

Anemia is a condition where the number of red blood cells or the amount of hemochrome in the peripheral blood has decreased; i.e., the number of red blood cells is 80% or less of the normal state or the amount of hemochrome is 12 g/dL or less.

In general, the total number of blood cells in blood, especially the number of hemoglobin, decreases with the progress of anemia, so that the ability to transport oxygen decreases to cause lack of oxygen in tissues. As a result, there are observed shortness of breath after exercise, palpitation, dizziness, tinnitus, heaviness of the head, headache, anorexia, constipation, diarrhea, feeling of weariness, coldness of limbs, cardiac palpitation, irregular mense, micturition disorder, sexual debility, difficult breathing during rest, fainting and angina pectoris-like symptoms.

Anemia symptoms have been known to be caused by various factors. In order to ameliorate symptoms involved with anemia, eating habits are reconsidered and dietary supplements and drugs are given.

However, in the method for ameliorating anemia by intake of foods, satisfactory effects cannot be expected without taking in iron-rich foods simultaneously with nutrients such as vitamins C, B6 and B12 and folic acid. Among pharmaceutical drugs prescribed for anemia symptoms, Ferromia, Ferrum, Fero-Gradumet, TETUCUR, Slow-Fe, Methycobal, Foliamin and Pydoxal can cause, after administration, adverse side effects such as vomiting, nausea, anorexia, stomach discomfort, stomachache, diarrhea, constipation rash, urticaria and itchy.

Therefore, for an anemia-ameliorating composition, studies have been conducted on ingredients contained in naturally occurring products which can be given with ease for a long time, which can be given safely and effortlessly, which involve no adverse side effects, and which have been taken in on a daily basis since long ago.

Use of medicated ginseng for amelioration of anemia has already been known (see JP-A Nos. 08-143465 and 2002-275086) and it has been found that its active ingredients are ginsenosides (see JP-A No. 2002-322068) and triterpene glycoside (see JP-A No. 2003-517016). JP-A No. 2002-322068 describes that the ginsenosides include not only saponins (glycosides) but also protopanaxadiol (PPD) and protopanaxatriol (PPT) which are aglycons remaining after removal of the sugar moiety.

However, there is no previous report about use of panaxadiol (PD) and panaxatriol (PT) for an anemia-ameliorating composition, which are formed after the side chains of the aglycons have been cyclized.

Furthermore, gouty arthritis caused by hyperuricemia has recently been a problem. In Japan, the number of hyperuricemia patients, who are likely to develop gout, is estimated to be about 5,000,000. As younger patients with hyperuricemia have increased, the number of hyperuricemia patients becomes twice or more that seen 20 years ago.

Uric acid is produced in the liver in an almost constant amount from purines from foods. Almost all the uric acid produced is filtered out to urine from the kidney in many cases, followed by excretion. However, when the balance between the amount of uric acid produced and the amount of uric acid excreted is lost due to certain factors (e.g., eating habits, alcohol drinking, stress, reduction in kidney functions, effects of drugs and genetic factors), the uric acid level in the body increases excessively, potentially leading to hyperuricemia. When the blood uric acid level exceeds 7.0 mg/dL as a result of increasing of the uric acid level in the body, such condition is determined as hyperuricemia. When hyperuricemia is not treated for a long time, an excessive amount of uric acid salts forms their crystals around joints and cartilage tissue, inducing gouty arthritis.

Currently, there are some pharmaceutical drugs for the treatment of hyperuricemia. After withdrawal of them, however, the recovered state is returned to the condition of hyperuricemia. Also, after administration, they cause adverse side effects such as fever, rash, hepatic disorder and abnormalities in kidney functions. Accordingly, keen demand has arisen for a therapeutic drug for hyperuricemia which can be given safely and effortlessly for a long time without adverse side effects.

Under such circumstances, much research has been made on plant-origin uric-acid-level-reducing compositions without adverse side effects. For example, JP-A No. 2005-187405 proposes a uric-acid-level-reducing agent containing as an active ingredient activated carbon made by using palm shell as a raw material. JP-A No. 2002-370980 proposes a uric-acid-level-reducing agent containing ginkgo leaf extract as an active ingredient and a food or beverage containing the uric-acid-level-reducing agent. JP-A No. 2002-212085 proposes a uric-acid-level-reducing agent containing as an active ingredient tea polyphenol derived from tea. JP-A No. 2006-16340 proposes a xanthine oxidase inhibitor, a blood-uric-acid-level-reducing agent, a hyperuricemia-preventing or -ameliorating agent, a gout-preventing agent, each containing pomegranate extract as an active ingredient, and a food or beverage, a pharmaceutical drug and a cosmetic, each containing these agents. JP-A No. 2007-153888 proposes an internal body purifying composition containing crude drugs such as *Panax notoginseng* and ginseng, and a food, a bathing agent, a cosmetic, a pharmaceutical preparation and a harmful metal excretion enhancer containing it, for the purpose of enhancing excretion of toxins from the body such as harmful substances and waste products (e.g., uric acid) which are formed through metabolism in the body. JP-A No. 09-208479 proposes a willow mixture for increasing and enhancing excretion of uric acid, which contains at least one of *Panax notoginseng* and *Panax* ginseng as well as a powdery material of plants belonging to the family Salicaceae. JP-A No. 03-9752 proposes a sauna using medical herb such as ginseng for the purpose of giving efficacy to symptoms such as gout. Proc. Symp. WAKAN-YAKU 16 (p. 188 (1983)) reports effects of long-term administration of medicated ginseng on the bodies of hyperlipemia patients, such as a change in the blood uric acid level.

SUMMARY OF THE INVENTION

The present invention aims to solve the above existing problems and achieve the following objects. Specifically, an object of the present invention is to provide: a neutral-fat-level-regulating agent, a cholesterol-level-regulating agent, a free-fatty-acid-level-regulating agent, an anti-obesity agent and a hyperlipemia-ameliorating agent, which have excellent neutral-fat-level-regulating effects, cholesterol-level-regulating effects, free-fatty-acid-level-regulating effects and anti-obesity effects and which are naturally occurring and highly safe and can be given as a food or beverage; an anemia-ameliorating composition which has excellent anemia-ameliorating effects and which is naturally occurring and highly safe and can be given as a food or beverage; a uric-acid-level-reducing composition which has excellent uric-acid-level-reducing effects, which can be given safely and effortlessly for a long time without adverse side effects, and which contributes to the prevention and amelioration of hyperuricemia; a food or beverage containing the neutral-fat-level-regulating agent, the cholesterol-level-regulating agent, the free-fatty-acid-level-regulating agent, the anti-obesity agent, the anemia-ameliorating composition and/or the uric-acid-level-reducing composition.

The present inventors conducted extensive studies to solve the above existing problems and have obtained the following findings: a neutral-fat-level-regulating agent, a cholesterol-level-regulating agent, a free-fatty-acid-level-regulating agent and an anti-obesity agent each containing at least one of protopanaxatriol, panaxatriol, protopanaxadiol and panaxadiol which are aglycons of dammarane-type saponins have excellent neutral-fat-level-regulating effects, cholesterol-level-regulating effects, free-fatty-acid-level-regulating effects and anti-obesity effects and are naturally occurring and highly safe and can be given as a food or beverage; an anemia-ameliorating composition containing panaxadiol and panaxatriol as active ingredients has excellent anemia-ameliorating effects and is naturally occurring and highly safe and can be given as a food or beverage; and a uric-acid-level-reducing composition containing as an active ingredient an acid-treated product residue obtained by hydrolyzing a plant belonging to the genus *Panax* of the family Araliaceae in the presence of an aqueous strong acid solution and a lower alcohol and filtrating the plant with the addition of water has excellent uric-acid-level-reducing effects, can be given safely and effortlessly for a long time without adverse side effects, and contributes to the prevention and amelioration of hyperuricemia. The present invention has been accomplished on the basis of these findings.

The present invention is based on the findings obtained by the present inventors. Means for solving the existing problems are as follows.

<1> A neutral-fat-level-regulating agent, a cholesterol-level-regulating agent, a free-fatty-acid-level-regulating agent or an anti-obesity agent, including:

at least one selected from the group consisting of protopanaxatriol, panaxatriol, protopanaxadiol and panaxadiol which are aglycons of dammarane-type saponins.

<2> The neutral-fat-level-regulating agent, the cholesterol-level-regulating agent, the free-fatty-acid-level-regulating agent or the anti-obesity agent according to <1>, wherein the aglycons are derived from a strong acid-treated product obtained by treating ginseng belonging to the family Araliaceae with a strong acid.

<3> The neutral-fat-level-regulating agent, the cholesterol-level-regulating agent, the free-fatty-acid-level-regulating agent or the anti-obesity agent according to <2>, wherein the strong acid-treated product is obtained by hydrolyzing the ginseng belonging to the family Araliaceae with an aqueous strong acid solution having a concentration of 0.01 mol/L to 4 mol/L in the presence of a lower alcohol.

<4> The neutral-fat-level-regulating agent, the cholesterol-level-regulating agent, the free-fatty-acid-level-regulating agent or the anti-obesity agent according to <3>, wherein an amount of the lower alcohol is 1% by volume to 80% by volume relative to a total amount of a hydrolyzation liquid.

<5> The neutral-fat-level-regulating agent, the cholesterol-level-regulating agent, the free-fatty-acid-level-regulating agent or the anti-obesity agent according to <3> or <4>, wherein the neutral-fat-level-regulating agent, the cholesterol-level-regulating agent, the free-fatty-acid-level-regulating agent or the anti-obesity agent is obtained through a process including: neutralizing a liquid obtained after the hydrolyzing; filtrating the neutralized liquid; and drying the residue.

<6> The neutral-fat-level-regulating agent, the cholesterol-level-regulating agent, the free-fatty-acid-level-regulating agent or the anti-obesity agent according to <5>, wherein the process further includes prior to the filtrating: adding water to the liquid obtained after the hydrolyzing to adjust a concentration of the lower alcohol therein to 0.05% by volume to 50% by volume.

<7> The neutral-fat-level-regulating agent, the cholesterol-level-regulating agent, the free-fatty-acid-level-regulating agent or the anti-obesity agent according to any one of <1> to <6>, wherein an amount of the neutral-fat-level-regulating agent, the cholesterol-level-regulating agent, the free-fatty-acid-level-regulating agent or the anti-obesity agent given per day is 1 mg to 300 mg.

<8> A hyperlipemia-ameliorating agent including: at least one selected from the group consisting of the neutral-fat-level-regulating agent, the cholesterol-level-regulating agent, the free-fatty-acid-level-regulating agent and the anti-obesity agent according to any one of <1> to <7>.

<9> An anemia-ameliorating composition including: panaxadiol and panaxatriol which serve as active ingredients.

<10> The anemia-ameliorating composition according to <9>, wherein the anemia-ameliorating composition has an effect of increasing human blood hematocrit level and an effect of increasing human mean corpuscular volume level.

<11> The anemia-ameliorating composition according to <9> or <10>, wherein the anemia-ameliorating composition is given per day in such an amount that at least 1 mg of the active ingredients is given.

<12> A uric-acid-level-reducing composition including: an acid-treated product residue of a plant belonging to the genus *Panax* of the family Araliaceae as an active ingredient, wherein the acid-treated product residue is obtained by hydrolyzing the plant belonging to the genus *Panax* of the family Araliaceae in the presence of an aqueous strong acid solution and a lower alcohol and filtrating the plant with the addition of water.

<13> The uric-acid-level-reducing composition according to <12>, wherein the plant belonging to the genus *Panax* of the family Araliaceae is *Panax notoginseng*.

<14> The uric-acid-level-reducing composition according to <12> or <13>, wherein the uric-acid-level-reducing composition is used as a blood-uric-acid-level-reducing agent, a hyperuricemia-preventing agent, a hyperuricemia-ameliorating agent, a gout-preventing agent and a gout-ameliorating agent.

<15> A food or beverage including:
at least one selected from the group consisting of: the neutral-fat-level-regulating agent, the cholesterol-level-regulating agent, the free-fatty-acid-level-regulating agent and the anti-obesity agent according to any one of <1> to <7>; the hyperlipemia-ameliorating agent according to <8>; the anemia-ameliorating composition according to any one of <9> to <11>; and the uric-acid-level-reducing composition according to any one of <12> to <14>.

The present invention can provide: a neutral-fat-level-regulating agent, a cholesterol-level-regulating agent, a free-fatty-acid-level-regulating agent, an anti-obesity agent and a hyperlipemia-ameliorating agent, which have excellent neutral-fat-level-regulating effects, cholesterol-level-regulating effects, free-fatty-acid-level-regulating effects and anti-obesity effects and which are naturally occurring and highly safe and can be given as a food or beverage; an anemia-ameliorating composition which has excellent anemia-ameliorating effects and which is naturally occurring and highly safe and can be given as a food or beverage; a uric-acid-level-reducing composition which has excellent uric-acid-level-reducing effects, which can be given safely and effortlessly for a long time without adverse side effects, and which contributes to the prevention and amelioration of hyperuricemia; and a food or beverage containing the neutral-fat-level-regulating agent, the cholesterol-level-regulating agent, the free-fatty-acid-level-regulating agent, the anti-obesity agent, the anemia-ameliorating composition and/or the uric-acid-level-reducing composition. These can solve the above existing problems and achieve the above objects.

DETAILED DESCRIPTION OF THE INVENTION (Neutral-Fat-Level-Regulating Agent, Cholesterol-Level-Regulating Agent, Free-Fatty-Acid-Level-Regulating Agent and Anti-Obesity Agent)

A neutral-fat-level-regulating agent, a cholesterol-level-regulating agent, a free-fatty-acid-level-regulating agent and an anti-obesity agent of the present invention each contain at least one selected from the group consisting of protopanaxatriol, panaxatriol, protopanaxadiol and panaxadiol; and, if necessary, further contains other ingredients.

<Protopanaxatriol, Panaxatriol, Protopanaxadiol and Panaxadiol>

Protopanaxatriol, panaxatriol, protopanaxadiol and panaxadiol are compounds belonging to dammarane-type triterpenes.

Protopanaxatriol, panaxatriol, protopanaxadiol and panaxadiol are aglycons each formed after the sugar moiety has been removed from a plant-origin saponin (glycoside).

The plant is not particularly limited and may be appropriately selected depending on the intended purpose. It is preferably ginseng belonging to the family Araliaceae, more preferably a plant belonging to the genus *Panax* of the family Araliaceae.

The plant belonging to the genus *Panax* of the family Araliaceae is not particularly limited and may be appropriately selected depending on the intended purpose. Examples thereof include *Panax notoginseng* (denshichi ninjin, also called sanshichi ninjin), *Panax ginseng* (otane ninjin, also called chousen ninjin or kourai ninjin), *Panax japonicus* (also called chikusetsu ninjin), *Panax quinquefolius* (also called seiyou ninjin or seiyou jin), *Panax vietnamensis, Panax pseudoginseng*, soushishiyou ninjin, *Panax wangianus*, kyouyouka ninjin (also called chikukonshichi), uyousanshichi, shuureika ninjin (also called chikusetus sanshichi), daiyousanshichi, gabisanshichi, *Panax stipuleanatus* (also called takusanshichi), *Panax trifolius* and *Panax zingiberensis* (also called kyoujyou sanshichi). These may be used alone or in combination.

Among them, *Panax ginseng* and *Panax notoginseng* are preferred. *Panax notoginsengis* particularly preferred since it can stably be obtained.

Saponins derived from the *Panax notoginseng* are not particularly limited and may be appropriately selected depending on the intended purpose. Examples thereof include ginsenoside-$Rg_1$, notoginsenoside-$R_1$, ginsenoside-Re, ginsenoside-$Rb_1$, ginsenoside-Rd and ginsenoside-Rc.

<<Method for Obtaining at Least One of Protopanaxatriol, Panaxatriol, Protopanaxadiol and Panaxadiol>>

The method for obtaining at least one of protopanaxatriol, panaxatriol, protopanaxadiol and panaxadiol is not particularly limited and may be appropriately selected depending on the intended purpose. Examples thereof include a method in which it is obtained by extracting the ginseng belonging to the family Araliaceae, a method in which it is obtained by enzymatically fermenting the ginseng belonging to the family Araliaceae, a method in which it is obtained by hydrolyzing the ginseng belonging to the family Araliaceae, and a method in which it is obtained through synthesis. Besides, commercially available products thereof may be used.

The ginseng belonging to the family Araliaceae may be used as is after it has been harvested from the natural world. However, since the ginseng belonging to the family Araliaceae contains more active ingredients in its roots and rhizome, it is preferable to use powder obtained by milling these roots and rhizome. In particular, from the viewpoint of efficiently conducting the below-described acid treatment, the ginseng belonging to the family Araliaceae used is preferably in the form of powder.

The method in which at least one of protopanaxatriol, panaxatriol, protopanaxadiol and panaxadiol is obtained by extracting the ginseng belonging to the family Araliaceae is not particularly limited and may be appropriately selected depending on the intended purpose. Examples thereof include a method by extracting the ginseng belonging to the family Araliaceae with water-ethanol solution, a supercritical extraction method, and a HPLC extraction method.

In the method by extracting the ginseng belonging to the family Araliaceae with water-ethanol solution, the ratio between water and ethanol in the water-ethanol solution is not particularly limited and may be appropriately selected depending on the intended purpose. The ratio of water:ethanol (V/V) is preferably 9:1 to 2:1, more preferably 3:1.

Among them, the method for obtaining at least one of protopanaxatriol, panaxatriol, protopanaxadiol and panaxadiol is preferably a method in which it is obtained by hydrolyzing the ginseng belonging to the family Araliaceae, more preferably a method in which the ginseng belonging to the family Araliaceae is hydrolyzed with an acid and at least one of protopanaxatriol, panaxatriol, protopanaxadiol and panaxadiol is obtained from the residue of the acid-treated product, particularly preferably a method in which at least one of protopanaxatriol, panaxatriol, protopanaxadiol and panaxadiol by the below-described production method.

Hydrolyzing the ginseng belonging to the family Araliaceae can efficiently produce at least one of protopanaxatriol, panaxatriol, protopanaxadiol and panaxadiol, which can exhibit excellent neutral-fat-level-regulating effects, cholesterol-level-regulating effects, free-fatty-acid-level-regulating effects and anti-obesity effects.

The acid-treated product residue can be obtained through a process including: hydrolyzing the ginseng belonging to the family Araliaceae in the presence of an aqueous strong acid solution and a lower alcohol at predetermined concentrations (hydrolyzing step); neutralizing the liquid obtained after the hydrolysis (neutralizing step); and filtrating the liquid with the addition of water (water-added filtration step). The residue separated in the water-added filtration step is purified (purifying step) and optionally dried (drying step) to thereby obtain at least one of protopanaxatriol, panaxatriol, protopanaxadiol and panaxadiol.

The above preferred production method will next be described in detail.

Notably, the ginseng belonging to the family Araliaceae may be used as is after it has been harvested from the natural world. Alternatively, the ginseng belonging to the family Araliaceae may be used after being subjected to pre-treatments such as washing, drying, cutting, smashing and milling which are appropriately combined together. In particular, use of the ginseng belonging to the family Araliaceae in the form of powder is preferred from the viewpoint of efficiently obtaining at least one of protopanaxatriol, panaxatriol, protopanaxadiol and panaxadiol.

—Hydrolyzing Step—

The hydrolyzing step is a step of hydrolyzing the ginseng belonging to the family Araliaceae in the presence of an aqueous strong acid solution and a lower alcohol at predetermined concentrations, to thereby form the acid-treated product.

The aqueous strong acid solution is not particularly limited, so long as it is an aqueous solution containing a strong acid, and may be appropriately selected depending on the intended purpose. The aqueous strong acid solution is preferably an aqueous solution containing an inorganic acid such as hydrochloric acid, phosphoric acid, sulfuric acid or nitric acid, more preferably an aqueous solution containing hydrochloric acid.

The concentration of the acid in the aqueous strong acid solution is not particularly limited and may be appropriately selected depending on the intended purpose. It is preferably 0.01 mol/L to 4 mol/L, more preferably 0.5 mol/L to 3 mol/L.

When the concentration of the acid in the aqueous strong acid solution is less than 0.01 mol/L, the hydrolysis is not sufficiently conducted and as a result at least one of protopanaxatriol, panaxatriol, protopanaxadiol and panaxadiol cannot efficiently be obtained in some cases. Whereas when it is more than 4 mol/L, the hydrolysis may excessively proceed and there may be a disadvantage in terms of cost.

When the concentration of the acid in the aqueous strong acid solution falls within the above preferred range, the hydrolysis is sufficiently conducted and as a result at least one of protopanaxatriol, panaxatriol, protopanaxadiol and panaxadiol can efficiently be obtained, which is advantageous.

The amount of the aqueous strong acid solution used is not particularly limited and may be appropriately selected depending on the intended purpose. It is preferably 2 times by volume to 20 times by volume relative to the ginseng belonging to the family Araliaceae. When the amount of the aqueous strong acid solution used is less than 2 times by volume relative to the ginseng belonging to the family Araliaceae, the ginseng belonging to the family Araliaceae is not immersed in the aqueous strong acid solution and as a result the hydrolysis cannot sufficiently be conducted. Whereas when it is more than 20 times by volume, there may be a disadvantage in terms of cost.

—Use of Lower Alcohol—

The hydrolysis is preferably conducted in the presence of a lower alcohol. Use of the lower alcohol can improve the affinity between the ginseng belonging to the family Araliaceae and the aqueous strong acid solution, to thereby allow the hydrolysis to proceed efficiently.

The lower alcohol is not particularly limited and may be appropriately selected depending on the intended purpose. It is preferably methanol, ethanol or propanol, with ethanol being preferred in terms of safety.

Notably, in this specification, the "lower alcohol" refers to alcohol compounds having 1 to 4 carbon atoms.

The amount of the lower alcohol used is not particularly limited and may be appropriately selected depending on the intended purpose. It is preferably 1% by volume to 80% by volume, more preferably 10% volume to 50% by volume, still more preferably 20% by volume to 40% by volume, relative to the total amount of the hydrolyzation liquid.

When the amount of the lower alcohol used is less than 1% by volume relative to the total amount of the hydrolyzation liquid, at least one of protopanaxatriol, panaxatriol, protopanaxadiol and panaxadiol cannot efficiently be obtained in some cases. Whereas when it is more than 80% by volume, at least one of protopanaxatriol, panaxatriol, protopanaxadiol and panaxadiol cannot efficiently be obtained and there may be a disadvantage in terms of cost.

When the amount of the lower alcohol used falls within the above preferred range, at least one of protopanaxatriol, panaxatriol, protopanaxadiol and panaxadiol can efficiently be obtained, which is advantageous.

Notably, the "total amount of the hydrolyzation liquid" refers to the total amount of the reaction liquid containing the aqueous strong acid solution and the lower alcohol.

—Total Amount of the Hydrolyzation Liquid—

The total amount of the reaction liquid containing the aqueous strong acid solution and the lower alcohol (the total amount of the hydrolyzation liquid) is not particularly limited and may be appropriately selected depending on the intended purpose. It is preferably 2 times by volume to 20 times by volume relative to the ginseng belonging to the family Araliaceae. When the total amount of the reaction liquid is less than 2 times by volume relative to the ginseng belonging to the family Araliaceae, the ginseng belonging to the family Araliaceae is not immersed in the reaction liquid and as a result the hydrolysis cannot sufficiently be conducted. Whereas when it is more than 20 times by volume, there may be a disadvantage in terms of cost.

—Temperature at which the Hydrolysis is Conducted—

The temperature at which the hydrolysis is conducted is not particularly limited and may be appropriately selected depending on the intended purpose. It is preferably 60° C. to 100° C., more preferably 70° C. to 90° C.

When the temperature at which the hydrolysis is conducted is less than 60° C., the hydrolysis is not sufficiently conducted and as a result at least one of protopanaxatriol, panaxatriol, protopanaxadiol and panaxadiol cannot efficiently be obtained in some cases. Whereas when it is more than 100° C., it is necessary to use special production facilities and as a result there may be a disadvantage in terms of cost.

When the temperature at which the hydrolysis is conducted falls within the above preferred range, the acid-treated product can efficiently be obtained and also at least one of protopanaxatriol, panaxatriol, protopanaxadiol and panaxadiol can efficiently be obtained, which is advantageous.

—Time for which the Hydrolysis is Conducted—

The time for which the hydrolysis is conducted is not particularly limited and may be appropriately selected depending on the intended purpose. It is preferably 30 min to 24 hours, more preferably 2 hours to 8 hours.

When the time for which the hydrolysis is conducted is shorter than 30 min, the hydrolysis is not sufficiently conducted and as a result at least one of protopanaxatriol, panaxatriol, protopanaxadiol and panaxadiol cannot efficiently be obtained in some cases. Whereas it is longer than 24 hours, the reaction may excessively proceed and there may be a disadvantage in terms of cost.

When the time for which the hydrolysis is conducted falls within the above preferred range, at least one of protopanaxatriol, panaxatriol, protopanaxadiol and panaxadiol can efficiently be obtained, which is advantageous.

—Neutralizing Step—

The neutralizing step is a step of neutralizing the liquid obtained in the hydrolyzing step.

The method for the neutralization is not particularly limited and may be a known method. Examples thereof include a method in which an aqueous solution of a strong base such as sodium hydroxide or potassium hydroxide is appropriately added to the liquid obtained after the hydrolysis. Notably, the pH of the liquid after the neutralization is not particularly limited and may be appropriately selected depending on the intended purpose. The pH thereof is preferably 5 to 8.

—Filtrating Step—

The filtrating step is a step of filtrating the liquid obtained in the hydrolyzing step with the addition of water, to thereby be separated into a filtrate and an acid-treated product residue. This step is preferably conducted since the amount of impurities can be made small.

The method for the filtration is not particularly limited and may be a known method. Notably, after the filtration, the acid-treated product residue may be repeatedly washed with water until the salts are completely removed.

—Water-Added Filtration—

When the lower alcohol is not used in the hydrolyzing step, the liquid obtained after the neutralization can be subjected to the filtration without any further treatment. However, when the lower alcohol is used in the hydrolyzing step, prior to the filtration, the concentration of the lower alcohol in the liquid obtained after the hydrolysis is preferably reduced with the addition of water, for the purpose of making at least one of protopanaxatriol, panaxatriol, protopanaxadiol and panaxadiol remain in the acid-treated product residue.

In this case, the amount of water to be added is not particularly limited and may be appropriately selected depending on the intended purpose. Although it is preferably more, water is more preferably added so that the concentration of the lower alcohol in the liquid obtained after the hydrolysis is 0.05% by volume to 50% by volume, still more preferably 30% by volume or less, particularly preferably 10% by volume or less.

When the concentration of the lower alcohol in the liquid obtained after the hydrolysis is higher than 50% by volume upon the filtration, at least one of protopanaxatriol, panaxatriol, protopanaxadiol and panaxadiol dissolves in the lower alcohol and is removed as the filtrate, so that the amount thereof in the residue disadvantageously decreases.

When the concentration of the lower alcohol in the liquid obtained after the hydrolysis falls within the above more preferred range, it is possible to further increase the amount of at least one of protopanaxatriol, panaxatriol, protopanaxadiol and panaxadiol contained in the residue, which is advantageous.

Although the acid-treated product residue obtained after the filtrating step may be used as at least one of protopanaxatriol, panaxatriol, protopanaxadiol and panaxadiol without any further treatment, it is preferable to further purify the acid-treated product residue in the below-described filtrating step from the viewpoint of obtaining high-purity protopanaxatriol, panaxatriol, protopanaxadiol and panaxadiol.

The acid-treated product residue may be directly used in the form of liquid, or may be dried in the below-described drying step before use.

—Purifying Step—

The method for purifying the acid-treated product residue is not particularly limited and may be appropriately selected depending on the intended purpose. Examples thereof include a method in which the acid-treated product residue is purified using a silica gel column.

The method in which the acid-treated product residue is purified using a silica gel column is not particularly limited and may be appropriately selected depending on the intended purpose. For example, the *Panax notoginseng* powder obtained through the acid hydrolysis is dissolved in ethanol to prepare an ethanol solution containing the powder at a concentration of 1% by mass to 5% by mass; the ethanol solution is treated with filter paper or a centrifuge to remove insoluble matter; the thus-treated solution is 5-fold to 10-fold concentrated with a rotary evaporator; and the concentrated liquid is applied to a glass column packed with silica gel (e.g., SILICA GEL 60N, product of KANTO CHEMICAL CO., LTD.) with chloroform:ethanol=10:1 (V/V) being used as an eluent (i.e., column separation/collection).

In the silica gel thin-layer chromatography using a developing solvent of chloroform:ethanol=10:1 (V/V), fractions corresponding to Rf values of 0.6, 0.4, 0.45 and 0.2 can be concentrated to obtain high-purity panaxadiol, panaxatriol, protopanaxadiol and protopanaxatriol, respectively.

—Drying Step—

The drying step is a step of drying the acid-treated product residue or at least one of protopanaxatriol, panaxatriol, protopanaxadiol and panaxadiol that have been purified.

The method for the drying is not particularly limited and may be a known method. Examples thereof include freeze drying, air-circulation drying, heating drying, reduced-pressure drying and spray drying.

<Amounts>

The amount of at least one of protopanaxatriol, panaxatriol, protopanaxadiol and panaxadiol contained in each of the neutral-fat-level-regulating agent, the cholesterol-level-regulating agent, the free-fatty-acid-level-regulating agent and the anti-obesity agent is not particularly limited and may be appropriately selected depending on the intended purpose, so long as the effects of the present invention are not impeded. Also, each of the neutral-fat-level-regulating agent, the cholesterol-level-regulating agent, the free-fatty-acid-level-regulating agent and the anti-obesity agent may be at least one of protopanaxatriol, panaxatriol, protopanaxadiol and panaxadiol.

<Other Ingredients>

The other ingredients are not particularly limited and may be appropriately selected depending on the intended purpose. For example, they may be selected from pharmacologically acceptable carriers depending on, for example, the dosage form of the neutral-fat-level-regulating agent, the cholesterol-level-regulating agent, the free-fatty-acid-level-regulating agent and the anti-obesity agent. Examples thereof include ethanol, water and starch.

When each of the neutral-fat-level-regulating agent, the cholesterol-level-regulating agent, the free-fatty-acid-level-regulating agent and the anti-obesity agent is used for the below-described food or beverage, the other ingredients are, for example, supplemental materials and additives. Also, the amount of the other ingredients is not particularly limited and may be appropriately selected depending on the intended purpose.

<Neutral-Fat-Level-Regulating Effects, Cholesterol-Level-Regulating Effects, Free-Fatty-Acid-Level-Regulating Effects and Anti-Obesity Effects>

The neutral-fat-level-regulating effects of the neutral-fat-level-regulating agent refer to effects of lowering the plasma neutral fat level when it is high and keeping the plasma neutral fat level when it is normal.

The cholesterol-level-regulating effects of the cholesterol-level-regulating agent refer to effects of lowering the plasma cholesterol level when it is high and keeping the plasma cholesterol level when it is normal.

The free-fatty-acid-level-regulating effects of the free-fatty-acid-level-regulating agent refer to effects of lowering the plasma free fatty acid level when it is high and keeping the plasma free fatty acid level when it is normal.

The anti-obesity effects of the anti-obesity agent refer to effects of lowering the plasma fat level when it is high, keeping the plasma fat level when it is normal, lowering the visceral fat level when it is high, keeping the visceral fat level when it is normal, lowering the body weight when it is large, and keeping the body weight when it is normal (see Japanese Patent (JP-B) No. 3794669). Here, the visceral fat is not particularly limited and may be appropriately selected depending on the intended purpose so long as it is fat of the viscera. Examples thereof include retroperitoneal fat, fat surrounding the epididymis, and fat surrounding the kidney.

<Intake>

The method, amount, frequency, time, and target of intake of each of the neutral-fat-level-regulating agent, the cholesterol-level-regulating agent, the free-fatty-acid-level-regulating agent and the anti-obesity agent are not particularly limited and may be appropriately selected depending on the intended purpose.

The method of intake thereof is not particularly limited and may be appropriately selected depending on the intended purpose. A method of orally giving each of them is preferred since users can easily continue to take in it.

The amount of intake thereof is not particularly limited and may be appropriately determined considering various factors of target individuals such as their age, body weight, constitution, symptoms and concomitant use of one or more drugs containing other active ingredients. The daily intake thereof is preferably 1 mg to 300 mg. The daily intake within this preferred range is advantageous in that it is possible to obtain neutral-fat-level-regulating effects, cholesterol-level-regulating effects, free-fatty-acid-level-regulating effects and anti-obesity effects.

The time of intake thereof is not particularly limited and may be appropriately selected depending on the intended purpose. In order to reduce intake-related bothers of users, the time of intake thereof should not be limited to a certain time such as the same time as a meal or after a meal. It is preferred that they exhibit their neutral-fat-level-regulating effects, cholesterol-level-regulating effects, free-fatty-acid-level-regulating effects and anti-obesity effects even when it is not given at the same time as a meal. However, so long as the form thereof is a dosage form which can be given as an ordinary food together with a meal without bothers, the neutral-fat-level-regulating effects, the cholesterol-level-regulating effects, the free-fatty-acid-level-regulating effects and the anti-obesity effects can be obtained without depending on the time when they are given. In other words, the time when they are given may be the same time as a meal.

Regarding animal species that can be targets of intake thereof, they are suitably applied to human. However, so long as the effects of them can be obtained, they also be applied to non-human animals such as mice, rats, hamsters, birds, dogs, cats, sheep, goats, bovine, pigs and monkeys.

<Use>

The neutral-fat-level-regulating agent, the cholesterol-level-regulating agent, the free-fatty-acid-level-regulating agent and the anti-obesity agent may be used alone or in combination of two or more thereof. Alternatively, they may be used in combination with one or more drugs containing other active ingredients. The neutral-fat-level-regulating agent, the cholesterol-level-regulating agent, the free-fatty-acid-level-regulating agent and/or the anti-obesity agent may be incorporated before use into one or more drugs containing other active ingredients.

<Application>

Since the neutral-fat-level-regulating agent, the cholesterol-level-regulating agent, the free-fatty-acid-level-regulating agent, and the anti-obesity agent each have excellent neutral-fat-level-regulating effects, cholesterol-level-regulating effects, free-fatty-acid-level-regulating effects and anti-obesity effects, they can suitably be used for the below-described hyperlipemia-ameliorating agent. Also, they can suitably be used for the below-described food or beverage.

(Hyperlipemia-Ameliorating Agent)

A hyperlipemia-ameliorating agent of the present invention contains at least one of the neutral-fat-level-regulating agent, the cholesterol-level-regulating agent, the free-fatty-acid-level-regulating agent and the anti-obesity agent; and, if necessary, further contains other ingredients.

<Neutral-Fat-Level-Regulating Agent, Cholesterol-Level-Regulating Agent, Free-Fatty-Acid-Level-Regulating Agent and Anti-Obesity Agent>

The amount of the at least one of the neutral-fat-level-regulating agent, the cholesterol-level-regulating agent, the free-fatty-acid-level-regulating agent and the anti-obesity agent is not particularly limited and may be appropriately selected depending on the intended purpose.

The hyperlipemia-ameliorating agent may contain only the at least one selected from the group consisting of the neutral-fat-level-regulating agent, the cholesterol-level-regulating agent, the free-fatty-acid-level-regulating agent and the anti-obesity agent, or may be the at least one selected from the group consisting of the hyperlipemia-ameliorating agent, the neutral-fat-level-regulating agent, the cholesterol-level-regulating agent, the free-fatty-acid-level-regulating agent and the anti-obesity agent.

<Other Ingredients>

The other ingredients are not particularly limited and may be appropriately selected depending on the intended purpose. For example, they may be selected from pharmacologically acceptable carriers depending on, for example, the dosage form of the hyperlipemia-ameliorating agent. Examples thereof include ethanol, water and starch. When the hyperlipemia-ameliorating agent is used for the below-described food or beverage, the other ingredients are, for example, supplemental materials and additives. Also, the amount of the other ingredients is not particularly limited and may be appropriately selected depending on the intended purpose.

<Use>

The hyperlipemia-ameliorating agent may be used alone or in combination with one or more drugs containing other active ingredients. The hyperlipemia-ameliorating agent may be incorporated before use into one or more drugs containing other active ingredients.

<Application>

The hyperlipemia-ameliorating agent can be applied to the prevention or treatment of, for example, arterial sclerosis, cardiac infarction, cerebral infarction, high blood pressure, kidney diseases, aortic aneurysm, diabetes, obesity and abnormality of functions of the thyroid. Also, it can suitably be used for the below-described food or beverage.

(Anemia-Ameliorating Composition)

An anemia-ameliorating composition of the present invention contains panaxadiol and panaxatriol as active ingredients; and, if necessary, further contains other ingredients.

The panaxadiol and the panaxatriol contained in the anemia-ameliorating composition can be obtained by similar methods to that described for the neutral-fat-level-regulating agent, the cholesterol-level-regulating agent, the free-fatty-acid-level-regulating agent or the anti-obesity agent. Preferred embodiments thereof are also similar thereto.

<Intake>

The method, amount, frequency, time, and target of intake of the anemia-ameliorating composition are not particularly limited and may be appropriately selected depending on the intended purpose.

The method of intake thereof is not particularly limited and may be appropriately selected depending on the intended purpose. A method of orally giving the anemia-ameliorating composition is preferred since users are easy to continue to take in it.

The amount of intake thereof is not particularly limited and may be appropriately determined considering various factors of target individuals such as their age, body weight, constitution, symptoms and concomitant use of one or more drugs containing other active ingredients. The daily intake thereof is preferably at least 1 mg, more preferably 2 mg to 20 mg. The daily intake within this preferred range is advantageous in that it is possible to ameliorate various symptoms accompanied by lack of oxygen in tissues as well as to improve intake suitability.

The frequency of intake thereof is not particularly limited and may be appropriately selected depending on the intended purpose. The anemia-ameliorating composition is preferably given once a day since such a frequency is convenient for users.

From this point of view, the anemia-ameliorating composition preferably contains the above active ingredient in an amount of at least 1 mg, more preferably 2 mg to 20 mg.

Regarding animal species that can be targets of intake thereof, the anemia-ameliorating composition is suitably applied to human. However, so long as the effects of the anemia-ameliorating composition can be obtained, the anemia-ameliorating composition may also be applied to non-human animals such as mice, rats, hamsters, birds, dogs, cats, sheep, goats, bovine, pigs and monkeys.

<Use>

The anemia-ameliorating composition may be used alone or in combination with one or more drugs containing other active ingredients. The anemia-ameliorating composition may be incorporated before use into one or more drugs containing other active ingredients.

<Application>

Since the anemia-ameliorating composition has excellent effects of increasing the hematocrit level and the mean corpuscular volume level, it can be suitably used for the prevention or amelioration of pathological conditions such as reduction in ability to transport oxygen due to a decrease in number of hemoglobin, shortness of breath after exercise due to lack of oxygen in tissues, palpitation, dizziness, tinnitus, heaviness of the head, headache, anorexia, constipation, diarrhea, feeling of weariness, coldness of limbs, cardiac palpitation, irregular mense, micturition disorder, sexual debility, difficult breathing during rest, fainting and angina pectoris-like symptoms. Also, the anemia-ameliorating composition can suitably be used for the below-described food or beverage.

(Uric-Acid-Level-Reducing Composition)

A uric-acid-level-reducing composition of the present invention contains as an active ingredient an acid-treated product residue obtained by hydrolyzing a plant belonging to the genus *Panax* of the family Araliaceae in the presence of an aqueous strong acid solution and a lower alcohol and filtrating the plant with the addition of water; and, if necessary, further contains other ingredients.

<Acid-Treated Product Residue of a Plant Belonging to the Genus *Panax* of the Family Araliaceae>

The acid-treated product residue of a plant belonging to the genus *Panax* of the family Araliaceae exhibits uric-acid-level-reducing effects superior to those of a plant belonging to the genus *Panax* of the family Araliaceae.

One possible reason for this is as follows. Specifically, when a plant belonging to the genus *Panax* of the family Araliaceae is treated with an acid, sapogenins (aglycons) such as panaxatriol, panaxadiol, protopanaxatriol and protopanaxadiol are formed as described above, and such sapogenins exhibit uric-acid-level-reducing effects as active ingredients.

The amount of the sapogenins contained in the acid-treated product residue is not particularly limited and may be appropriately selected depending on the intended purpose. It is preferably 3% by mass or more, more preferably 5% by mass or more, particularly preferably 10% by mass or more.

The amount of the sapogenins can be measured through, for example, liquid chromatography.

The amount of the acid-treated product residue contained in the uric-acid-level-reducing composition is not particularly limited and may be appropriately selected depending on the intended purpose. Also, the uric-acid-level-reducing composition may be the acid-treated product residue itself.

<Other Ingredients>

The other ingredients are not particularly limited and may be appropriately selected depending on the intended purpose, so long as the effects of the present invention are not impeded.

Also, the amount of the other ingredients contained in the uric-acid-level-reducing composition is not particularly limited and may be appropriately selected depending on the intended purpose.

<Production Method>

As described above, the acid-treated product residue of a plant belonging to the genus *Panax* of the family Araliaceae is obtained by hydrolyzing a plant belonging to the genus *Panax* of the family Araliaceae in the presence of an aqueous strong acid solution and a lower alcohol and filtrating the plant with the addition of water.

In particular, the following production method is preferably used from the viewpoint of efficiently obtaining the acid-treated product residue.

Specifically, the acid-treated product residue can be obtained through a process including: hydrolyzing a plant belonging to the genus *Panax* of the family Araliaceae in the presence of an aqueous strong acid solution and a lower alcohol at predetermined concentrations (hydrolyzing step); neutralizing the liquid obtained after the hydrolysis (neutralizing step); filtrating the liquid with the addition of water (water-added filtration step); and drying the residue separated through the filtration (drying step).

The hydrolyzing step, the neutralizing step, the water-added filtrating step and the drying step can be performed similar to the hydrolyzing step, the neutralizing step, the water-added filtrating step and the drying step in the method for obtaining at least one of protopanaxatriol, panaxatriol, protopanaxadiol and panaxadiol described for the neutral-fat-level-regulating agent, the cholesterol-level-regulating agent, the free-fatty-acid-level-regulating agent and the anti-obesity agent. Their preferred embodiments are also similar thereto.

<Intake>

The method, amount, frequency, time, and target of intake of the uric-acid-level-reducing composition are not particularly limited and may be appropriately selected depending on the intended purpose.

The method of intake thereof is not particularly limited and may be appropriately selected depending on the intended purpose. A method of orally giving the uric-acid-level-reducing composition is preferred since users are easy to continue to take in it.

The amount of intake thereof is not particularly limited and may be appropriately determined considering various factors of target individuals such as their age, body weight, constitution, symptoms and concomitant use of one or more drugs containing other active ingredients. The daily intake thereof is preferably at least 1 mg, more preferably 10 mg to 1,000 mg, still more preferably 20 mg to 500 mg, particularly preferably 30 mg to 300 mg.

The frequency of intake thereof is not particularly limited and may be appropriately selected depending on the intended purpose. The uric-acid-level-reducing composition is preferably given once a day since such a frequency is convenient for users and also users are easier to continue to take in it.

Regarding animal species that can be targets of intake thereof, the uric-acid-level-reducing composition is suitably applied to human. However, so long as the effects of the uric-acid-level-reducing composition can be obtained, the uric-acid-level-reducing composition may also be applied to non-human animals such as mice, rats, hamsters, birds, dogs, cats, sheep, goats, bovine, pigs and monkeys. When the targets of intake thereof are humans, the uric-acid-level-reducing composition exhibits particularly excellent uric-acid-level-reducing effects on those with hyperuricemia whose uric acid levels are higher than 7.0 mg/dL, which is advantageous.

<Use>

The uric-acid-level-reducing composition may be used alone or in combination with one or more drugs containing other active ingredients. The uric-acid-level-reducing composition also may be incorporated before use into one or more drugs containing other active ingredients.

<Application>

The uric-acid-level-reducing composition can be used for various applications such as drugs, quasi drugs, common foods, healthy foods, healthy beverages, health-promoting foods, food additives, feeds and feed additives. The uric-acid-level-reducing composition can be provided as dry powder, or prepared into any other forms such as a liquid preparation, a tablet, powder, granules, a sugar-coated tablet, a capsule, a suspension, an emulsion, an ampul and an injection.

When the uric-acid-level-reducing composition is formed into a pharmaceutical drug, it can be used as a therapeutic drug such as a blood-uric-acid-level-reducing agent, a hyperuricemia-preventing agent, a hyperuricemia-ameliorating agent, a gout-preventing agent and a gout-ameliorating agent.

The formulation method of a pharmaceutical drug is not particularly limited and may be appropriately selected depending on the intended purpose. The formulation of a pharmaceutical drug can be performed by a known formulation technique. Appropriate additives may also be added to the pharmaceutical drug.

(Food or Beverage)

A food or beverage of the present invention contains at least one of the neutral-fat-level-regulating agent, the cholesterol-level-regulating agent, the free-fatty-acid-level-regulating agent, the anti-obesity agent, the hyperlipemia-ameliorating agent, the anemia-ameliorating composition and the uric-acid-level-reducing composition; and, if necessary, further contains other ingredients.

Here, "food or beverage" refers to those which are less harmful to human health and which are given orally or through the gastrointestinal tract in the ordinary social life. They are not limited to foods, drugs and quasi drugs within the administrative boundaries, but include a wide variety of orally-given common foods, healthy foods, health-promoting foods, quasi drugs and drugs.

The amount of the at least one of the neutral-fat-level-regulating agent, the cholesterol-level-regulating agent, the free-fatty-acid-level-regulating agent, the anti-obesity agent, the hyperlipemia-ameliorating agent, the anemia-ameliorating composition and the uric-acid-level-reducing composition incorporated into the food or beverage is not particularly limited and may be appropriately selected depending on the type of the food or beverage so long as the effects of the present invention are not impeded.

The food or beverage may contain only the at least one selected from the group consisting of the neutral-fat-level-regulating agent, the cholesterol-level-regulating agent, the free-fatty-acid-level-regulating agent, the anti-obesity agent, the hyperlipemia-amelioratingagent, the anemia-ameliorating composition and the uric-acid-level-reducing composition, or may be the at least one selected from the group consisting of the neutral-fat-level-regulating agent, the cholesterol-level-regulating agent, the free-fatty-acid-level-regulating agent, the anti-obesity agent, the hyperlipemia-ameliorating agent, the anemia-ameliorating composition and the uric-acid-level-reducing composition.

<Type of Food or Beverage>

The type of the food or beverage is not particularly limited and may be appropriately selected depending on the intended purpose. Examples thereof include beverages such as refreshing beverages, carbonated beverages, energy beverages, fruit beverages and lactic beverage; frozen desserts such as ice cream, ice sherbet and ice shavings; noodles such as buckwheat noodles, wheat noodles, vermicelli, coats of Chinese dumplings, coats of pork dumplings, Chinese noodles and instant noodles; snacks such as candies, gum, chocolate, tabletted snacks, munches, biscuits, jelly, jam, cream, baked confectionery and bread; marine products such as crab, salmon, Japanese littleneck, tuna, sardine, shrimps, prawns, bonito, mackerel, whale, oyster, saury, squid, bloody clam, scallop, abalone, sea chestnut, salmon caviar and Sulculus diversicolor supertexta; marine/livestock processed foods such as fish minced and steamed, ham and sausage; dairy products such as processed milk and fermented milk; fats and oils or processed foods thereof such as salad oil, Tempura oil, margarine, mayonnaise, shortening, whip cream and dressing; seasonings such as sauce and basting; retort pouch foods such as curry, stew, Oyako-don (a bowl of rice topped with boiled chicken and eggs), rice porridge, Zosui (rice soup), Chuka-don (a bowl of rice with a chop-suey-like mixture on it), Katsu-don (a rice bowl with pork cutlets), Ten-don (a tempura rice bowl), Una-don (an eel rice bowl), hayashi rice (hashed beef with rice), Oden (a dish containing several ingredients such as boiled eggs and radish), mapo doufu, Gyu-don (a beef rice bowl), meat sauce, egg soup, rice omelet, Chinese dumplings, pork dumplings, hamburger steak and meat balls; healthy foods in various forms and dietary supplements; and pharmaceutical drugs and quasi drugs.

<Other Ingredients>

The other ingredients are not particularly limited and may be appropriately selected depending on the intended purpose. Examples thereof include supplemental materials or additives commonly used for the production of foods and beverages.

The supplemental materials or additives are not particularly limited and may be appropriately selected depending on the intended purpose. Examples thereof include glucose, fructose, sucrose, maltose, sorbitol, stevioside, rubusoside, corn syrup, lactose, citric acid, tartaric acid, malic acid, succinic acid, lactic acid, L-ascorbic acid, dl-α-tocopherol, sodium erythorbate, glycerin, propylene glycol, glycerin fatty acid esters, polyglycerin fatty acid esters, sucrose fatty acid esters, sorbitan fatty acid esters, gum arabic, carrageenan, casein, gelatin, pectin, agar, B vitamins, nicotinic-acid amide, calcium pantothenate, amino acids, calcium salts, dyes, perfumes and preservatives.

The amount of the other ingredients contained in the composition is not particularly limited and may be appropriately selected depending on the intended purpose.

EXAMPLES

The present invention will next be described in more detail by way of Examples, which should not be construed as limiting the present invention thereto.

Production Example 1

Production of Hyperlipemia-Ameliorating Agent 5.9% by mass hydrochloric acid (6,666 mL) and 99.9% by mass aqueous ethanol solution (3,334 mL) were added to *Panax notoginseng* powder (1,000 g, product of MATSUURA YAKUGYO CO., LTD.) containing saponins such as ginsenoside-$Rg_1$, notoginsenoside-$R_1$, ginsenoside-Re, ginsenoside-$Rb_1$, ginsenoside-Rd and ginsenoside-Rc. The resultant suspension was hydrolyzed with heating for 6 hours at 80° C. to prepare an aglycon-containing extract. Then, the pH of the aglycon-containing extract was adjusted to 6.7 with 6.6M aqueous sodium hydroxide solution to reduce the ethanol concentration, followed by suction filtration.

The residue was dried with heating under reduced pressure, to thereby obtain a strong acid-treated *Panax notoginseng* product containing aglycons.

Example 1

Study on Hyperlipemia-Ameliorating Effects

<Method>

—Preparation of Feed—

Protopanaxatriol (PPT) (product of Funakoshi Corporation), panaxatriol (PT) (product of Funakoshi Corporation), protopanaxadiol (PPD) (product of Funakoshi Corporation) and panaxadiol (PD) (product of Funakoshi Corporation) were each added to feed CE2 (product of CLEA Japan, Inc.) so that the concentration thereof was 0.05% by mass.

Similarly, the strong acid-treated *Panax notoginseng* product (Production Example 1) and *Panax notoginseng* powder (product of MATSUURA YAKUGYO CO., LTD.) were each added to feed CE2 (product of CLEA Japan, Inc.) so that the concentration thereof was 1.0% by mass.

Feed CE2 (product of CLEA Japan, Inc.) containing no other additives was used as feed for the control group.

—Intake—

Type 2-diabetes model mice KK-Ay/Ta Jc1 (male, 4 weeks old, 8 mice/group, product of CLEA Japan, Inc.) were preliminarily bred for 7 days. Thereafter, they were bred for 5 days with the above-prepared feed CE2, containing no other additives or containing PPT, PT, PPD, PD, the strong acid-treated *Panax notoginseng* product or *Panax notoginseng* powder.

Notably, the group given the feed CE2 containing *Panax notoginseng* powder is a comparative group.

—Measurements of Neutral Fat Level, Total Cholesterol Level and Free Fatty Acid Level in Plasma and Measurements of Visceral Fat Level and Body Weight—

The mice bred for 5 days in the above-described manner were measured for the body weight after an overnight fast. The blood was collected from them. The collected blood sample was used to measure the plasma neutral-fat level with GLUCOSE CII-TEST WAKO (product of Wako Pure Chemical Industries, Ltd.), the plasma total-cholesterol level with CHOLESTEROL E-TEST WAKO (product of Wako Pure Chemical Industries, Ltd.) and the plasma free-fatty-acid level with TRIGLYCERIDE E-TEST WAKO (product of Wako Pure Chemical Industries, Ltd.). In addition, retroperitoneal fat, fat surrounding the epididymis, and fat surrounding the kidney were sampled and weighed. The total mass thereof was used as the visceral fat level. The above-measured plasma neutral-fat level, plasma total-cholesterol level, plasma free-fatty-acid level, visceral fat level and body weight were verified using the Dunnett's multiple test. A p value of 0.05 or lower was considered statistically significant.

<Results>

—Effects of Regulating Plasma Neutral-Fat Level—

The plasma neutral-fat levels measured are shown in Table 1 and 2.

TABLE 1

| Intake group | Control group (additive-free) | 0.05% by mass PPT | 0.05% by mass PT | 0.05% by mass PPD | 0.05% by mass PD |
|---|---|---|---|---|---|
| Neutral fat level (average mg/dL ± SD) | 407.3 ± 20.9 | 138.5 ± 25.3*** | 163 ± 32.8*** | 151.4 ± 26.9*** | 180.7 ± 34.2** |

**p < 0.01,
***p < 0.001

TABLE 2

| Intake group | Comparative group (1.0% by mass *Panax notoginseng* powder) | 1.0% by mass strong acid-treated *Panax notoginseng* product |
|---|---|---|
| Neutral fat level (average mg/dL ± SD) | 389.6 ± 59.5 | 148.1 ± 56.0*** |

***p < 0.001

As is clear from Tables 1 and 2, the intake groups given protopanaxatriol, panaxatriol, protopanaxadiol, panaxadiol and the strong acid-treated *Panax notoginseng* product were found to exhibit the neutral fat level-regulating effects significantly superior to that of the control group. In contrast, the comparative group given *Panax notoginseng* powder was not found to exhibit the neutral fat level-regulating effect clearly superior to that of the control group.

—Effects of Regulating Plasma Cholesterol Level—

The plasma cholesterol levels measured are shown in Tables 3 and 4.

TABLE 3

| Intake group | Control group (additive-free) | 0.05% by mass PPT | 0.05% by mass PT | 0.05% by mass PPD | 0.05% by mass PD |
|---|---|---|---|---|---|
| Total cholesterol level (average mg/dL ± SD) | 195.5 ± 10.7 | 128.3 ± 17.8* | 102.9 ± 16.7** | 123.2 ± 19.6* | 101.5 ± 15.6** |

*p < 0.05,
**p < 0.01

TABLE 4

| Intake group | Comparative group (1.0% by mass *Panax notoginseng* powder) | 1.0% by mass strong acid-treated *Panax notoginseng* product |
|---|---|---|
| Total cholesterol level (average mg/dL ± SD) | 179.3 ± 37.8 | 131.3 ± 19.9* |

*p < 0.05

As is clear from Tables 3 and 4, the intake groups given protopanaxatriol, panaxatriol, protopanaxadiol, panaxadiol and the strong acid-treated *Panax notoginseng* product were found to exhibit the cholesterol level-regulating effects significantly superior to that of the control group. In contrast, the comparative group given *Panax notoginseng* powder was not found to exhibit the cholesterol level-regulating effect clearly superior to that of the control group.

—Effects of Regulating Plasma Free-Fatty-Acid Level—

The plasma free-fatty-acid levels measured are shown in Tables 5 and 6.

TABLE 5

| Intake group | Control group (additive-free) | 0.05% by mass PPT | 0.05% by mass PT | 0.05% by mass PPD | 0.05% by mass PD |
|---|---|---|---|---|---|
| Free fatty acid level (average mEq/L ± SD) | 1.95 ± 0.3 | 0.93 ± 0.08* | 0.84 ± 0.07* | 0.81 ± 0.08* | 1.04 ± 0.12* |

*p < 0.05

TABLE 6

| Intake group | Comparative group (1.0% by mass *Panax notoginseng* powder) | 1.0% by mass strong acid-treated *Panax notoginseng* product |
|---|---|---|
| Free fatty acid level (average mEq/L ± SD) | 1.81 ± 0.47 | 0.98 ± 0.05* |

*p < 0.05

As is clear from Tables 5 and 6, the intake groups given protopanaxatriol, panaxatriol, protopanaxadiol, panaxadiol and the strong acid-treated *Panax notoginseng* product were found to exhibit the free fatty acid level-regulating effects significantly superior to that of the control group. In contrast, the comparative group given *Panax notoginseng* powder was not found to exhibit the free fatty acid level-regulating effect clearly superior to that of the control group.

—Anti-Obesity Effects—

The amounts of visceral fat measured are shown in Tables 7 and 8.

TABLE 7

| Intake group | Control group (additive-free) | 0.05% by mass PPT | 0.05% by mass PT | 0.05% by mass PPD | 0.05% by mass PD |
|---|---|---|---|---|---|
| Visceral fat level (average g ± SD) | 8.2 ± 1.0 | 5.5 ± 1.3* | 5.9. ± 1.2* | 5.9 ± 1.3* | 5.5 ± 1.6* |

*p < 0.05

TABLE 8

| Intake group | Comparative group (1.0% by mass *Panax notoginseng* powder) | 1.0% by mass strong acid-treated *Panax notoginseng* product |
|---|---|---|
| Visceral fat level (average g ± SD) | 7.8 ± 2.8 | 5.3 ± 1.9* |

*p < 0.05

As is clear from Tables 7 and 8, significant reduction in the visceral fat level was found in the intake groups given protopanaxatriol, panaxatriol, protopanaxadiol, panaxadiol and the strong acid-treated *Panax notoginseng* product as compared with the control group. In contrast, clear reduction in the visceral fat level was not found in the comparative group given *Panax notoginseng* powder as compared with the control group.

The body weights measured are shown in Tables 9 and 10.

TABLE 9

| Intake group | Control group (additive-free) | 0.05% by mass PPT | 0.05% by mass PT | 0.05% by mass PPD | 0.05% by mass PD |
|---|---|---|---|---|---|
| Body weight (average g/±SD) | 52.3 ± 4.2 | 45.3 ± 2.2* | 43.9 ± 2.8** | 46.8 ± 2.6* | 47.3 ± 1.9* |

*p < 0.05,
**p < 0.01

TABLE 10

| Intake group | Comparative group (1.0% by mass Panax notoginseng powder) | 1.0% by mass strong acid-treated Panax notoginseng product |
|---|---|---|
| Body weight (average g/±SD) | 55.3 ± 3.7 | 47 ± 2.9* |

*p < 0.05

As is clear from Tables 9 and 10, significant reduction in body weight was found in the intake groups given protopanaxatriol, panaxatriol, protopanaxadiol, panaxadiol and the strong acid-treated *Panax notoginseng* product as compared with the control group. In contrast, clear reduction in body weight was not found in the comparative group given *Panax notoginseng* powder as compared with the control group.

Example 2-1

A capsule was charged with 1.0 g of crystalline cellulose containing 0.6% by mass of panaxadiol (product of LKT Laboratories, Inc.) and 1.4% by mass of panaxatriol (product of LKT Laboratories, Inc.) (the total amount of panaxadiol and panaxatriol: 20.0 mg) to prepare an anemia-ameliorating composition of Example 2-1.

Comparative Example 2-1

In the same manner as in Example 2-1 except that a capsule was charged with 1.0 g of crystalline cellulose containing none of panaxadiol and panaxatriol, an anemia-ameliorating composition of Comparative Example 2-1 (hereinafter referred to as "control preparation") was prepared.

<Test for Anemia-Ameliorating Effects>

Twenty-one healthy subjects were measured for hematocrit (Ht) (%) and mean corpuscular volume (MCV) (fl) and categorized into two groups so that the averages of the Ht and MCV were nearly equal between the groups. In the fasting state in the morning, each of the healthy subjects of one group was given one capsule of the control preparation and each of those of the other group was given one capsule of the anemia-ameliorating composition of Example 2-1. This treatment was continued for 4 weeks.

<Test Results>

The hematocrit (Ht) level of the healthy subjects before and after the intake of the capsule was measured by the following method.

Specifically, it was measured by the red blood cell pulse wave detection method, which is a typical measurement method, using AUTOMATED HEMATOLOGY ANALYZER XE-2100 (product of SYSMEX CORPORATION).

—Measurements of Hematocrit Level—

Figure 1:
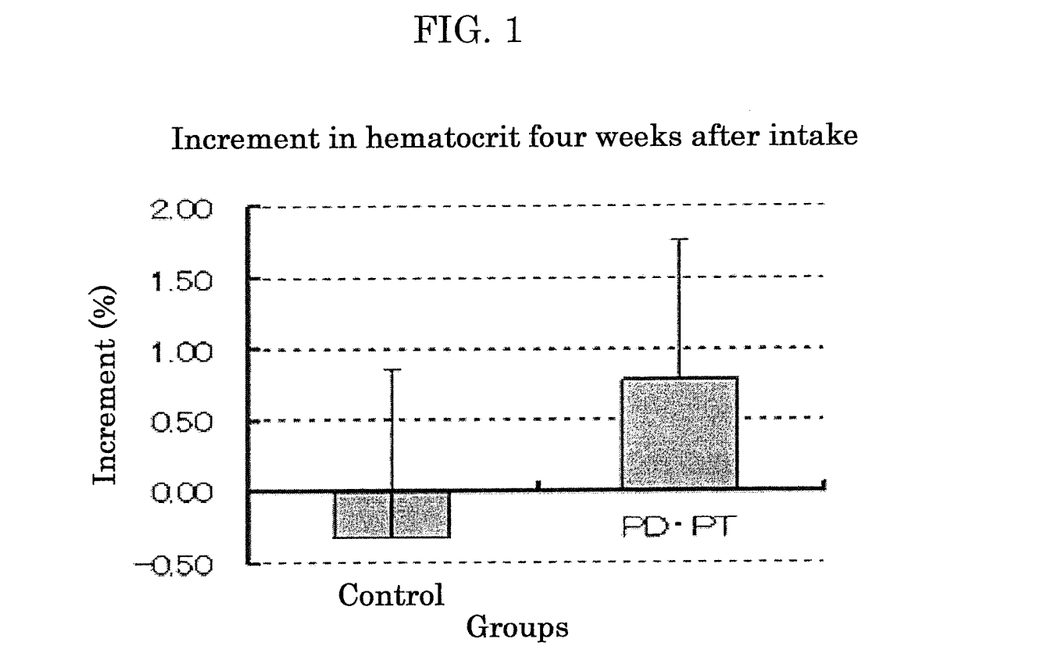
FIG. 1 is graph of hematocrit (Ht) levels measured four weeks after the intake of a capsule.

Table 11 and FIG. 1 show the hematocrit (Ht) levels measured before and after the intake of the capsule. A hematocrit is an index for the proportion of red blood cells contained in a certain amount of blood. The low hematocrit level means thin blood which may be indicative of anemia. The intake of the anemia-ameliorating composition of Example 2-1 increased the Ht within the normal range, confirming the anemia-ameliorating effects. Notably, in these results, a significant level p in the t-test is lower than 0.05.

TABLE 11

Hematocrit (Ht)

Unit: %

| Group | Before intake | 4 weeks after intake | Increment in Ht | Group | Before intake | 4 weeks after intake | Increment in Ht |
|---|---|---|---|---|---|---|---|
| Control | 42.5 | 42.9 | 0.4 | PD · PT | 47.1 | 48.3 | 1.2 |
|  | 45.2 | 45.6 | 0.4 |  | 42 | 42.4 | 0.4 |
|  | 48.8 | 48.1 | −0.7 |  | 41.6 | 44.8 | 3.2 |
|  | 42.5 | 41.6 | −0.9 |  | 47.3 | 47.8 | 0.5 |
|  | 47.5 | 47.7 | 0.2 |  | 45.2 | 45.7 | 0.5 |
|  | 42.3 | 42.5 | 0.2 |  | 39.1 | 39.2 | 0.1 |
|  | 36.2 | 36.5 | 0.3 |  | 44.9 | 46.1 | 1.2 |
|  | 48.7 | 45.3 | −3.4 |  | 45.4 | 46.3 | 0.9 |
|  | 44.1 | 44.3 | 0.2 |  | 43.9 | 44.7 | 0.8 |
|  | 40.2 | 40.3 | 0.1 |  | 42.2 | 41.3 | −0.9 |
|  |  |  |  |  | 44.3 | 44.9 | 0.6 |
| Average | 43.80 | 43.48 | −0.32 | Average | 43.91 | 44.68 | 0.77 |
| SD |  |  | 1.17 | SD |  |  | 0.99 |

Result of t-test of increment in Ht: 0.0342
In Table 11, SD denotes Standard Deviation.

The mean corpuscular volume (MCV) level of the healthy subjects before and after the intake of the capsule was measured by the following method.

Specifically, a blood sample was collected from each subject and applied to AUTOMATED HEMATOLOGY ANALYZER XE-2100 (product of SYSMEX CORPORATION) for measuring the mean corpuscular volume (MCV) level.

—Measurements of Mean Corpuscular Volume (MCV) Level—

Figure 2:
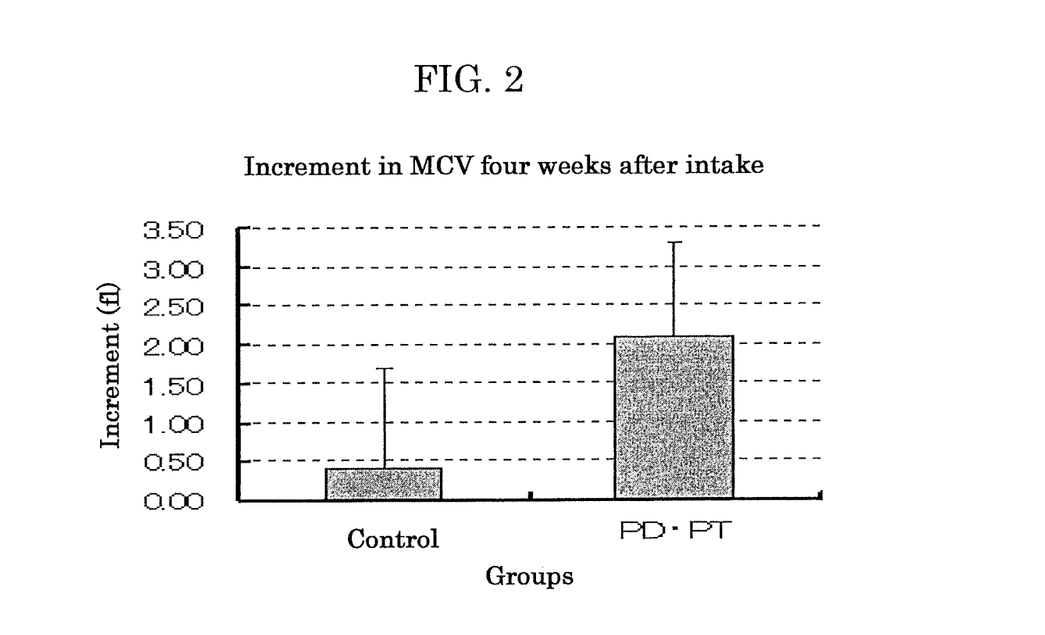
FIG. 2 is a graph of mean corpuscular volume (MCV) levels measured four weeks after the intake of a capsule.

Table 12 and FIG. 2 show the mean corpuscular volume (MCV) levels measured before and after the intake of the capsule. A MCV is an average of the volumes of red blood cells, and the low MCV is an index for anemia. The intake of the anemia-ameliorating composition of Example 2-1 increased the MCV within the normal range, confirming the anemia-ameliorating effects. Notably, in these results, a significant level p in the t-test is lower than 0.01.

TABLE 12

Mean corpuscular volume (MCV)

Unit: fl

| Group | Before intake | 4 weeks after intake | Increment in MCV | Group | Before intake | 4 weeks after intake | Increment in MCV |
|---|---|---|---|---|---|---|---|
| Control | 99 | 99 | 0 | PD · PT | 93 | 96 | 3 |
|  | 89 | 88 | −1 |  | 95 | 97 | 2 |
|  | 96 | 97 | 1 |  | 93 | 96 | 3 |
|  | 98 | 96 | −2 |  | 93 | 97 | 4 |
|  | 95 | 95 | 0 |  | 90 | 92 | 2 |
|  | 96 | 97 | 1 |  | 88 | 90 | 2 |
|  | 95 | 95 | 0 |  | 98 | 98 | 0 |
|  | 97 | 98 | 1 |  | 94 | 97 | 3 |
|  | 90 | 92 | 2 |  | 98 | 98 | 0 |
|  | 90 | 92 | 2 |  | 93 | 95 | 2 |
|  |  |  |  |  | 98 | 100 | 2 |
| Average | 94.5 | 94.9 | 0.4 | Average | 93.9 | 96.0 | 2.1 |
| SD |  |  | 1.26 | SD |  |  | 1.2 |

Result of t-test of increment in MCV: 0.0059
In Table 12, SD denotes Standard Deviation.

<Preparation of Uric-Acid-Level-Reducing Composition>

Example 3-1

0.48 L of hydrochloric acid (35.0% by mass to 37.0% by mass: product of Wako Pure Chemical Industries, Ltd.), 1.52

L of distilled water, and 1 L of 99.5% ethanol (product of Wako Pure Chemical Industries, Ltd.) were added to *Panax notoginseng* powder (300 g) and the resultant mixture was stirred and heated at 80° C. for 6 hours.

Subsequently, the pH of the obtained reaction mixture was adjusted to 7.0 with the addition of 5M aqueous sodium hydroxide solution, and 12.5 L of distilled water was added thereto. The resultant solution was separated through filtration into a filtrate and a residue.

The residue was freeze-dried to obtain 52.0 g of a uric-acid-level-reducing composition of Example 3-1, which was made of the residue of a acid-treated *Panax notoginseng* product (yield: 17.3%).

Comparative Example 3-1

The same *Panax notoginseng* powder as used in Example 3-1 was used as a uric-acid-level-reducing composition of Comparative Example 3-1.

<1$^{st}$ Test on Uric-Acid-Level-Reducing Effects>
—Test Method—

Twenty adults were measured for blood uric acid level and categorized into two groups so that the average of the blood uric acid levels was nearly equal between the groups. In the fasting state in the morning, each of the adults of one group was once given a capsule containing 1.0 g of the uric-acid-level-reducing composition of Comparative Example 3-1 (*Panax notoginseng* powder) and each of those of the other group was once given a capsule containing 173 mg of the uric-acid-level-reducing composition of Example 3-1 (strong acid-treated *Panax notoginseng* product) (which is equivalent to 1.0 g of *Panax notoginseng* powder). This treatment was continued for 2 weeks.

—Test Results—

As is understood from Table 13, the uric acid level was reduced by only 0.2 mg/dL after the 2-week intake from the uric acid level measured before intake in the *Panax notoginseng* powder group given the uric-acid-level-reducing composition of Comparative Example 3-1. In contrast, in the acid-treated *Panax notoginseng* product residue group given the uric-acid-level-reducing composition of Example 3-1, the uric acid level was considerably reduced; i.e., by 0.66 mg/dL, after the 2-week intake from the uric acid level measured before intake.

Statistical analysis was conducted using the Student's t-test on the differences between the uric acid levels before intake and the uric acid levels after the 2-week intake in the *Panax notoginseng* powder group and the acid-treated *Panax notoginseng* product residue group. As a result, a significant level P was found to be 0.02, indicating that a statistically significant difference was observed for the difference between the uric acid level before intake and the uric acid level after the 2-week intake in the acid-treated *Panax notoginseng* product residue group.

TABLE 13

| | Comp. Ex. 1: *Panax notoginseng* powder group | | | | Ex. 1: Acid-treated *Panax notoginseng* product residue group | | |
|---|---|---|---|---|---|---|---|
| | Uric acid level (mg/dL) | | | | Uric acid level (mg/dL) | | |
| Subject | Before intake | After 2-week intake | Difference | Subject | Before intake | After 2-week intake | Difference |
| 1 | 4.4 | 4.1 | 0.3 | 11 | 7.1 | 6.5 | 0.6 |
| 2 | 6.4 | 6.4 | 0 | 12 | 7.6 | 6.3 | 1.3 |
| 3 | 5.2 | 5.0 | 0.2 | 13 | 5.1 | 5.4 | −0.3 |

TABLE 13-continued

| | Comp. Ex. 1: *Panax notoginseng* powder group | | | | Ex. 1: Acid-treated *Panax notoginseng* product residue group | | |
|---|---|---|---|---|---|---|---|
| | Uric acid level (mg/dL) | | | | Uric acid level (mg/dL) | | |
| Subject | Before intake | After 2-week intake | Difference | Subject | Before intake | After 2-week intake | Difference |
| 4 | 7.1 | 6.9 | 0.2 | 14 | 6.3 | 5.6 | 0.7 |
| 5 | 6.6 | 6.3 | 0.3 | 15 | 7.2 | 6.8 | 0.4 |
| 6 | 6.1 | 5.9 | 0.2 | 16 | 6.3 | 5.4 | 0.9 |
| 7 | 8.5 | 8.5 | 0 | 17 | 5.9 | 5.0 | 0.9 |
| 8 | 7.3 | 6.5 | 0.8 | 18 | 6.5 | 5.3 | 1.2 |
| 9 | 2.6 | 2.1 | 0.5 | 19 | 5.7 | 5.3 | 0.4 |
| 10 | 5.7 | 6.2 | −0.5 | 20 | 3.9 | 3.4 | 0.5 |
| Avg. | 5.99 | 5.79 | 0.2 | Avg. | 6.16 | 5.5 | 0.66 |

<Test on Prevention and Amelioration of Hyperuricemia>
—Test Method—

The subjects of the acid-treated *Panax notoginseng* product residue group given the uric-acid-level-reducing composition of Example 3-1 for the evaluation of the uric-acid-level-reducing effects were categorized into the following two groups (1) and (2), each of which was measured for uric acid level in the following manner.

(1) 4-Week Intake Group (Subjects 11 to 15)

The subjects of this group received the uric-acid-level-reducing composition of Example 3-1 for another 2 weeks after the test on the uric-acid-level-reducing effects (2-week continuous intake); i.e., they received it every day for 4 weeks in total.

(2) Post-Withdrawal 2-Week Group (Subjects 16 to 20)

The subjects of this group were withdrawn from the intake after the test on the uric-acid-level-reducing effects (2-week continuous intake); i.e., they did not receive the uric-acid-level-reducing composition of Example 3-1 for the subsequent two weeks.

—Test Results—

Each of the subjects of the (1) 4-week intake group and the (2) post-withdrawal 2-week group was measured for uric acid level after the test. The results are shown in Table 14.

As is understood from Table 14, the (1) 4-week intake group was found to exhibit uric acid levels significantly lower than those of the (2) post-withdrawal 2-week group.

That is, the (2) post-withdrawal 2-week group could not keep low uric acid levels (the uric acid level increased by 0.6 mg/dL on average) when comparing the uric acid level at 2 weeks from the beginning of intake with the uric acid level at the end of the test (after 2 weeks passed from the withdrawal of the intake). The (1) 4-week intake group could keep low uric acid levels (the uric acid level decreased by 0.18 mg/dL on average) when comparing the uric acid level at 2 weeks from the beginning of intake with the uric acid level at the end of the test (after 4 weeks passed from the beginning of intake).

Notably, statistical analysis was conducted using the Student's t-test on the difference between the uric acid level at 2 weeks from the beginning of intake and the uric acid level at the end of the test (after 4 weeks passed from the beginning of intake) in the 4-week intake group and the difference between the uric acid level at 2 weeks from the beginning of intake and the uric acid level at the end of the test (after 2 weeks passed from the withdrawal of the intake) in the post-withdrawal 2-week group. As a result, a significant level P was found to be 0.05, indicating that a statistically significant difference was observed for the uric-acid-level reducing effects.

As described above, since the continuous intake of the uric-acid-level-reducing composition of Example 3-1 can suppress an increase in uric acid level and also the withdrawal of the intake of the uric-acid-level-reducing composition results in an increase in uric acid level, presumably, the uric-acid-level-reducing composition of the present invention can contribute to the prevention and amelioration of hyperuricemia.

TABLE 14

| Subject | | Uric acid level (mg/dL) | | | | |
|---|---|---|---|---|---|---|
| | | Before intake | After 2 weeks from the intake | After 4 weeks from the intake | After 2 weeks passed from the withdrawal | Difference between 2 weeks and 4 weeks |
| (1) Group | 11 | 7.1 | 6.5 | 6.8 | — | −0.3 |
| | 12 | 7.6 | 6.3 | 6.4 | — | −0.1 |
| | 13 | 5.1 | 5.4 | 4.8 | — | 0.6 |
| | 14 | 6.3 | 5.6 | 5.2 | — | 0.4 |
| | 15 | 7.2 | 6.8 | 6.5 | — | 0.3 |
| | Avg. | 6.7 | 6.1 | 5.9 | — | 0.2 |
| (2) Group | 16 | 6.3 | 5.4 | — | 7.2 | −1.8 |
| | 17 | 5.9 | 5.0 | — | 5.2 | −0.2 |
| | 18 | 6.5 | 5.3 | — | 5.6 | −0.3 |
| | 19 | 5.7 | 5.3 | — | 5.7 | −0.4 |
| | 20 | 3.9 | 3.4 | — | 3.7 | −0.3 |
| | Avg. | 5.7 | 4.9 | — | 5.5 | −0.6 |

<$2^{nd}$ Test on Uric-Acid-Level-Reducing Effects>

The test on uric-acid-level-reducing effects was conducted using, as subjects, adults having a blood uric acid level of higher than 7.0 mg/dL which is an index for hyperuricemia (hyperuricemia group) and adults having a blood uric acid level of 7.0 mg/dL or lower (normal uric-acid-level group).

Example 3-2

Preparation of High-Content Agent

A capsule was charged with 1.0 g of crystalline cellulose containing 180 mg of the acid-treated *Panax notoginseng* product residue obtained in Example 3-1, to thereby prepare a uric-acid-level-reducing composition of Example 3-2 (hereinafter may be referred to as "high-content agent").

Example 3-3

Preparation of Low-Content Agent

A capsule was charged with 1.0 g of crystalline cellulose containing 45 mg of the acid-treated *Panax notoginseng* product residue obtained in Example 3-1, to thereby prepare a uric-acid-level-reducing composition of Example 3-3 (hereinafter may be referred to as "low-content agent").

Comparative Example 3-2

Preparation of Placebo

In the same manner as in Examples 3-2 and 3-3 except that a capsule was charged with 1.0 g of crystalline cellulose free of the acid-treated *Panax notoginseng* product residue obtained in Example 3-1, a uric-acid-level-reducing composition of Comparative Example 3-2 (hereinafter may be referred to as "placebo").

—Test Method—

The subjects tested were 12 adults having a blood uric acid level of higher than 7.0 mg/dL which is an index for hyperuricemia (hyperuricemia group: subjects 59 to 70) and 38 adults having a blood uric acid level of 7.0 mg/dL or lower (normal uric-acid-level group: subjects 21 to 58). The subjects of the hyperuricemia group and the normal uric-acid-level group were measured for blood uric acid level. Each of the groups was further categorized into three groups so that the average of the uric acid levels was nearly equal among the groups: a placebo group (subjects 21 to 33 or subjects 59 to 63), a low-content group (subjects 46 to 58 or subjects 68 to 70) and a high-content group (subjects 34 to 45 or subjects 64 to 67). In the fasting state in the morning, the placebo group was given once the uric-acid-level-reducing composition of Comparative Example 3-2, the low-content group was given once the uric-acid-level-reducing composition of Example 3-3, and the high-content group was given the uric-acid-level-reducing composition of Example 3-2. This treatment was continued for 12 weeks.

—Test Results—

The results of the normal uric-acid-level group are shown in Table 15, and the results of the hyperuricemia group are shown in Table 16.

As is understood from Table 15, in the normal uric-acid-level group where the subjects have a blood uric acid level of 7.0 mg/dL or lower, considerable change was not observed between the blood uric acid level before intake and the blood uric acid level after the 12-week intake.

In contrast, as is understood from Table 16, in the placebo group of the hyperuricemia group where the subjects have a blood uric acid level of higher than 7.0 mg/dL, the blood uric acid level increased by 0.36 mg/dL after the 12-week intake from the blood uric acid level measured before intake. In the low-content group given the uric-acid-level-reducing composition of Example 3-3, the blood uric acid level decreased by 0.47 mg/dL after the 12-week intake from the blood uric acid level measured before intake. Also, when statistical analysis was conducted using the Student's t-test on the measurement results, a significant level P was found to be 0.10, indicating that slight uric-acid-level-reducing effects were observed. In the high-content group given the uric-acid-level-reducing composition of Example 3-2, the blood uric acid level decreased by 0.6 mg/dL after the 12-week intake from the blood uric acid level measured before intake. Also, when statistical analysis was conducted using the Student's t-test on the measurement results, a significant level P was found to be 0.04, indicating that a statistically significant difference was observed for the uric-acid-level-reducing effects.

Notably, no adverse side effects were observed in the subjects of all the groups during the 12-week intake. In addition, they did not feel any resistance to the intake. These results indicate that the present test composition can continuously be given safely and effortlessly, and can effectively reduce the uric acid level especially in those having high blood uric acid levels.

TABLE 15

Normal uric-acid-level group (uric acid level ≤7.0 mg/dL)

| | Comp. Ex. 2: Placebo group | | | | Ex. 2: High-content group | | | | Ex. 3: Low-content group | | |
|---|---|---|---|---|---|---|---|---|---|---|---|
| | Uric acid level (mg/dL) | | | | Uric acid level (mg/dL) | | | | Uric acid level (mg/dL) | | |
| Subject | Before intake | After 12-week intake | Difference | Subject | Before intake | After 12-week intake | Difference | Subject | Before intake | After 12-week intake | Difference |
| 21 | 5.7 | 6.4 | −0.7 | 34 | 5.0 | 5.2 | −0.2 | 46 | 5.3 | 4.9 | 0.4 |
| 22 | 3.6 | 3.3 | 0.3 | 35 | 6.1 | 6.4 | −0.3 | 47 | 6.0 | 5.7 | 0.3 |
| 23 | 5.5 | 7.1 | −1.6 | 36 | 4.6 | 4.6 | 0.0 | 48 | 5.7 | 5.9 | −0.2 |
| 24 | 6.0 | 4.6 | 1.4 | 37 | 6.3 | 7.8 | −1.5 | 49 | 5.5 | 5.5 | 0.0 |
| 25 | 6.3 | 6.5 | −0.2 | 38 | 5.5 | 5.1 | 0.4 | 50 | 6.0 | 5.8 | 0.2 |
| 26 | 5.8 | 5.5 | 0.3 | 39 | 6.8 | 6.1 | 0.7 | 51 | 6.6 | 6.4 | 0.2 |
| 27 | 6.9 | 5.8 | 1.1 | 40 | 6.2 | 6.0 | 0.2 | 52 | 5.7 | 6.7 | −1.0 |
| 28 | 2.6 | 3.4 | −0.8 | 41 | 4.2 | 3.9 | 0.3 | 53 | 4.3 | 4.2 | 0.1 |
| 29 | 4.2 | 4.3 | −0.1 | 42 | 5.2 | 5.9 | −0.7 | 54 | 3.8 | 4.0 | −0.2 |
| 30 | 5.5 | 5.8 | −0.3 | 43 | 2.6 | 3.4 | −0.8 | 55 | 5.0 | 5.1 | −0.1 |
| 31 | 5.6 | 6.8 | −1.2 | 44 | 6.1 | 6.5 | −0.4 | 56 | 6.1 | 5.7 | 0.4 |
| 32 | 5.3 | 5.0 | 0.3 | 45 | 5.6 | 5.2 | 0.4 | 57 | 5.5 | 5.6 | −0.1 |
| 33 | 5.1 | 4.6 | 0.5 | | | | | 58 | 5.0 | 4.7 | 0.3 |
| Avg. | 5.24 | 5.32 | −0.08 | Avg. | 5.35 | 5.51 | −0.16 | Avg. | 5.42 | 5.40 | 0.02 |

TABLE 16

Hyperuricemia group (uric acid level >7.0 mg/dL)

| | Comp. Ex. 2: Placebo group | | | | Ex. 2: High-content group | | | | Ex. 3: Low-content group | | |
|---|---|---|---|---|---|---|---|---|---|---|---|
| | Uric acid level (mg/dL) | | | | Uric acid level (mg/dL) | | | | Uric acid level (mg/dL) | | |
| Subject | Before intake | After 12-week intake | Difference | Subject | Before intake | After 12-week intake | Difference | Subject | Before intake | After 12-week intake | Difference |
| 59 | 7.1 | 7.1 | 0.0 | 64 | 7.6 | 7.1 | 0.5 | 68 | 7.6 | 6.4 | 1.2 |
| 60 | 7.5 | 7.9 | −0.4 | 65 | 7.9 | 7.0 | 0.9 | 69 | 8.0 | 7.1 | 0.9 |
| 61 | 8.4 | 8.6 | −0.2 | 66 | 7.3 | 7.5 | −0.2 | 70 | 7.7 | 8.4 | −0.7 |
| 62 | 7.8 | 8.8 | −1.0 | 67 | 8.5 | 7.3 | 1.2 | | | | |
| 63 | 7.9 | 8.1 | −0.2 | | | | | | | | |
| Avg. | 7.74 | 8.10 | −0.36 | Avg. | 7.83 | 7.23 | 0.60 | Avg. | 7.77 | 7.30 | 0.47 |

The neutral-fat-level-regulating agent, the cholesterol-level-regulating agent, the free-fatty-acid-level-regulating agent, the anti-obesity agent and the hyperlipemia-ameliorating agent of the present invention have excellent neutral-fat-level-regulating effects, cholesterol-level-regulating effects, free-fatty-acid-level-regulating effects and anti-obesity effects, and thus are effective in the prevention or treatment of, for example, arterial sclerosis, cardiac infarction, cerebral infarction, high blood pressure and kidney diseases.

The anemia-ameliorating composition of the present invention has excellent effects of increasing the blood hematocrit level and increasing the mean corpuscular volume level, and thus is effective in the prevention or amelioration of a decrease in ability to transport oxygen due to a decrease in number of hemoglobin, shortness of breath after exercise due to lack of oxygen in tissues, palpitation, dizziness, tinnitus, heaviness of the head, headache, anorexia, constipation, diarrhea, feeling of weariness, coldness of limbs, cardiac palpitation, irregular mense, micturition disorder, sexual debility, difficult breathing during rest, fainting and angina pectoris-like symptoms.

The uric-acid-level-reducing composition of the present invention reduces the blood uric acid level and can be given safely and effortlessly for a long time without adverse side effects as well as contributes to the prevention and amelioration of hyperuricemia, and thus can suitably used as a blood-uric-acid-level-reducing agent, a hyperuricemia-preventing agent, a hyperuricemia-ameliorating agent, a gout-preventing agent and a gout-ameliorating agent.

Furthermore, the neutral-fat-level-regulating agent, the cholesterol-level-regulating agent, the free-fatty-acid-level-regulating agent, the anti-obesity agent, the hyperlipemia-ameliorating agent, the anemia-ameliorating agent and the uric-acid-level-reducing composition each are naturally occurring and highly safe, and thus can suitably used in foods or beverages.

What is claimed is:

1. A method for treating hyperuricemia or gout by reducing uric acid levels in a subject in need thereof comprising:
   administering to said subject a composition comprising an acid-treated product residue of a plant belonging to the genus *Panax* of the family Araliaceae as an active ingredient,
   wherein the acid-treated product residue is obtained by hydrolyzing the plant belonging to the genus *Panax* of the family Araliaceae in the presence of an aqueous strong acid solution and a lower alcohol and filtrating the plant with the addition of water.

2. The method according to claim 1, wherein the plant belonging to the genus *Panax* of the family Araliaceae is *Panax notoginseng*.

3. The method according to claim 1, wherein the uric-acid-level-reducing composition is used as a blood-uric-acid-level-reducing agent, a hyperuricemia-ameliorating agent, and a gout-ameliorating agent.

4. The method according to claim 1, wherein said composition is included in a food or beverage.

* * * * *